United States Patent [19]

Treuner et al.

[11] 4,386,199
[45] May 31, 1983

[54] CEPHALOSPORINS HAVING AN IMINO SUBSTITUTED PIPERAZINDIONCARBONYLAMINO ACYL SIDECHAIN

[75] Inventors: Uwe D. Treuner; Hermann Breuer, both of Regensburg, Fed. Rep. of Germany

[73] Assignee: E. R. Squibb & Sons, Inc., Princeton, N.J.

[21] Appl. No.: 259,876

[22] Filed: May 4, 1981

Related U.S. Application Data

[63] Continuation of Ser. No. 109,384, Jan. 3, 1980, abandoned, which is a continuation of Ser. No. 950,891, Oct. 12, 1978, abandoned.

[51] Int. Cl.³ ............................................ C07D 501/56
[52] U.S. Cl. ..................... 542/420; 544/21; 544/25; 544/27; 544/28
[58] Field of Search ............... 544/27; 542/420; 424/246

[56] References Cited

U.S. PATENT DOCUMENTS 4,147,693 4/1979 Konig et al. ................... 424/246
4,182,762 1/1980 Preiss ............................. 424/250
4,200,576 4/1980 Feyen et al. ................... 424/246

OTHER PUBLICATIONS

Burger, Medicinal Chemistry, 3rd Ed., (1970), pub. by Wiley-Interscience, p. 391.

Primary Examiner—Paul M. Coughlan, Jr.
Attorney, Agent, or Firm—Lawrence S. Levinson; Stephen B. Davis

[57] ABSTRACT

Cephalosporins of the formula

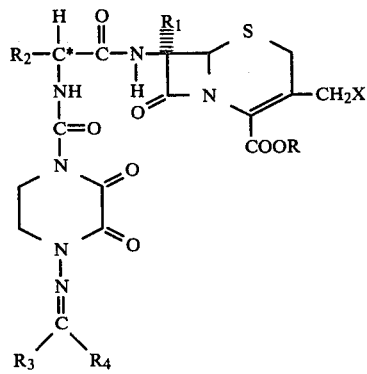

wherein R is hydrogen, sodium, potassium, or certain ester groups; $R_1$ is in the α-configuration and is hydrogen or methoxy; $R_2$ is hydrogen, lower alkyl, cycloalkyl, cycloalkenyl, cycloalkadienyl, substituted or unsubstituted phenyl, benzyl, phenethyl, thienyl, furyl, or pyridyl, or 2-amino-4-thiazolyl; $R_3$ is lower alkyl or substituted or unsubstituted phenyl, benzyl, phenethyl, thienyl, or furyl; $R_4$ is hydrogen or lower alkyl; and X is hydrogen,

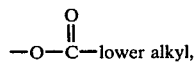

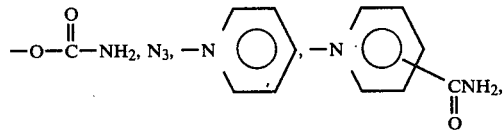

—O—lower alkyl, or certain substituted or unsubstituted heterothio groups; are disclosed. These compounds possess useful antibacterial activity.

6 Claims, No Drawings

CEPHALOSPORINS HAVING AN IMINO SUBSTITUTED PIPERAZINDIONCARBONYLAMINO ACYL SIDECHAIN

This is a continuation of application Ser. No. 109,384, filed Jan. 3, 1980, now abandoned, which is a continuation of application Ser. No. 950,891, filed Oct. 12, 1978, now abandoned.

BACKGROUND OF THE INVENTION

Saikawa et al. in U.S. Pat. No. 4,087,424 disclose penicillin and cephalosporin compounds having a substituted piperazindioncarbonylamino acyl sidechain. Cephalosporins having an (N-alkyl piperazindioncarbonylamino) substituent on the 2-position carbon atom of a phenylacetamido sidechain are specifically disclosed as compounds 60-71.

Bayer in Belgian Pat. No. 836,022 disclose penicillin and cephalosporin compounds having an imino substituted imidazoledioncarbonylamino group at the 2-position carbon atom of a phenylacetamido, cyclohexenylacetamido, or cyclohexadienylacetamido acyl sidechain.

SUMMARY OF THE INVENTION

This invention is directed to cephalosporins of the formula

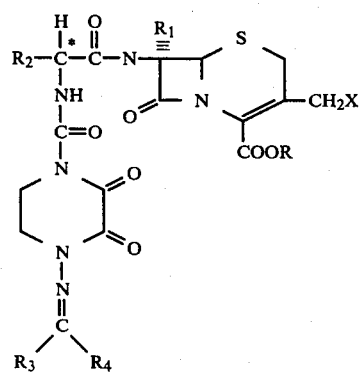

R represents hydrogen, sodium, potassium, t-butyl, benzyl, p-methoxybenzyl, p-nitrobenzyl, diphenylmethyl, 2,2,2-trichloroethyl, trimethylsilyl, —CH$_2$—O—lower alkyl,

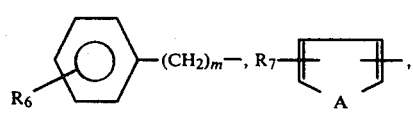

R$_1$ is in the α-configuration and is hydrogen or methoxy.

R$_2$ represents hydrogen, lower alkyl, cycloalkyl, cycloalkenyl, cycloalkadienyl,

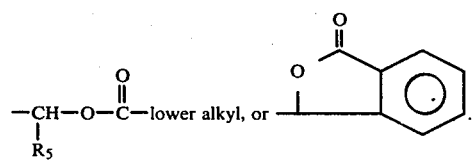

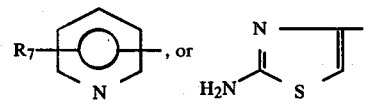

wherein R$_6$ is hydrogen, methyl, ethyl, methoxy, ethoxy, hydroxy, Cl, or Br; m is zero, 1 or 2; A is O or S; and R$_7$ is hydrogen, methyl, ethyl, Cl or Br.

R$_3$ represents lower alkyl,

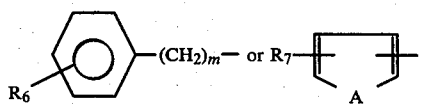

wherein R$_6$, R$_7$, m and A are as defined above.

R$_4$ represents hydrogen or lower alkyl.

R$_5$ represents hydrogen or lower alkyl.

X represents hydrogen,

—O—C(O)—lower alkyl, N$_3$, —O—C(O)—NH$_2$, —O—lower alkyl,

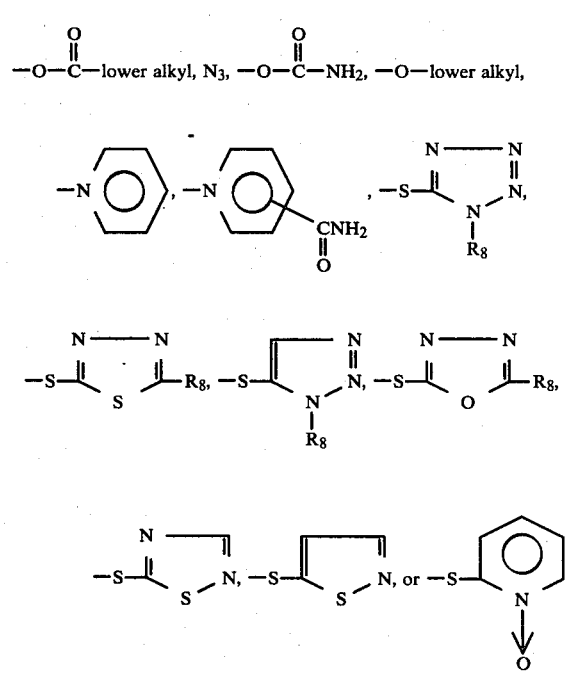

R$_8$ represents hydrogen, lower alkyl, —(CH$_2$)$_n$—COOR$_9$, —(CH$_2$)$_n$—SO$_3$R$_9$, or —(CH$_2$)$_n$—N(CH$_3$)$_2$ wherein n is an integer from 1 to 4 and R$_9$ is hydrogen, sodium, or potassium.

When X is pyridinium or carbamoyl substituted pyridinium, the compounds can be structurally represented as having the formula

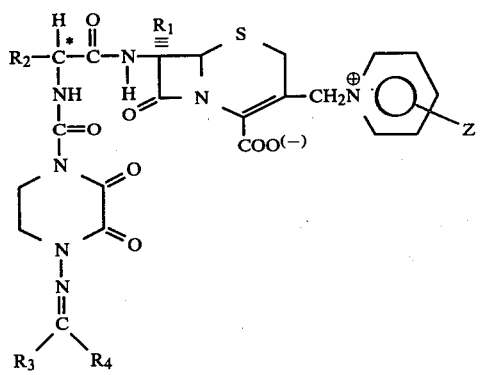

(Ia)

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbons containing 1 to 4 carbons, e.g. methyl, ethyl, i-propyl, t-butyl, etc.

Cycloalkyl refers to groups having 3 to 7 carbons in the ring, i.e. cyclopropyl, cyclobutyl, cyclopentyl, cyclohexyl, and cycloheptyl. The term cycloalkenyl represent rings having 5 to 7 carbons with one double bond, i.e. cyclopentenyl, cyclohexenyl, etc. The term cycloalkadienyl represents a ring having 6 or 7 carbons with two double bonds located at various positions such as 1,4-cyclohexadienyl which is preferred.

The compounds of formula I can be prepared by several methods. For example, when X is hydrogen,

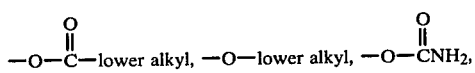

or heterothio, an α-amino compound of the formula

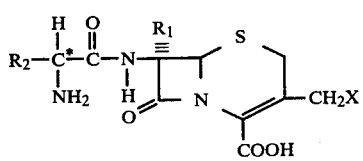
(II)

preferably in the form of its trifluoroacetic acid salt can be reacted with an acid chloride of the formula

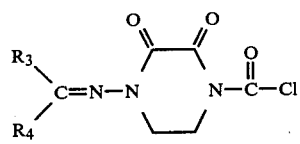
(III)

to yield the corresponding free acid compounds of formula I.

The α-amino intermediate of formula II can be prepared by various means such as by acylating a 7-amino cephalosporin of the formula

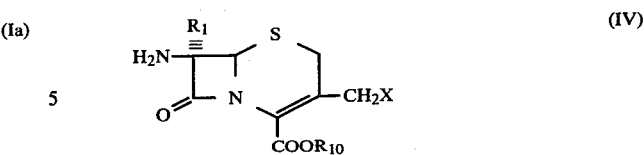
(IV)

wherein $R_{10}$ is a readily removable ester group such as diphenylmethyl, benzyl, substituted benzyl, t-butyl, etc.; $R_1$ is hydrogen or methoxy, and X is hydrogen,

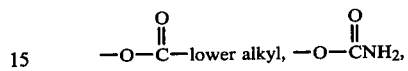

or heterothio, with a substituted α-amino acid of the formula

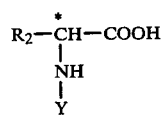
(V)

wherein Y is a protecting group such as

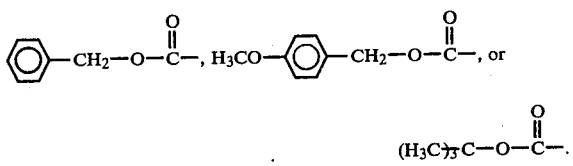

The α-amino protecting group and the ester group $R_{10}$ are then removed by treating the resulting cephalosporin with trifluoroacetic acid and anisole. The α-amino compounds of formula II are taught in various U.S. Patents as note for example U.S. Pat. Nos. 3,641,021; 3,796,801; 3,813,388; 3,978,051, 4,061,852; 4,000,134; 3,989,697; 3,989,693; 4,088,815; 4,088,816; etc. and Belgian Pat. No. 833,640.

The piperazindione acid chloride of formula III is prepared by reacting a hydrazine of the formula

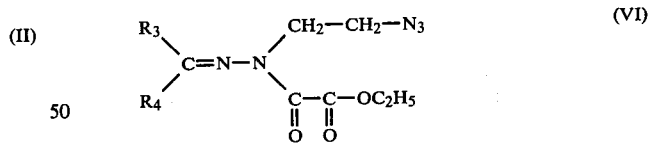
(VI)

with hydrogen in the presence of Lindar catalyst to yield the piperazindione of the formula

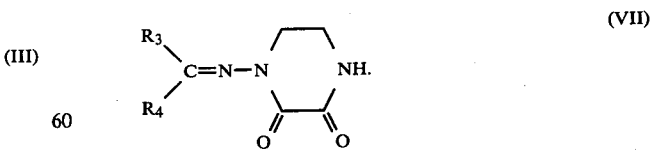
(VII)

The compound of formula VII can be treated with phosgene to yield the acid chloride of formula III directly. Alternatively, the compound of formula VII is treated with a silylating agent such as trimethylsilyl chloride or N-methyl-O-trimethylsilyltrifluoroacetamide to yield a mixture of

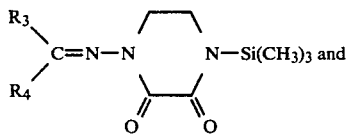
(VIII)

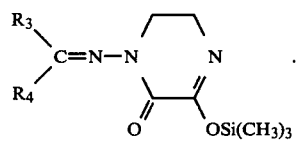
(IX)

This mixture is then treated with phosgene to yield the acid chloride of formula III.

The intermediate of formula VI can be prepared according to the following reaction sequence. An aldehyde or ketone of the formula

(X)

is reacted with a hydrazine of the formula

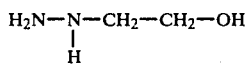
(XI)

to yield the compound of the formula

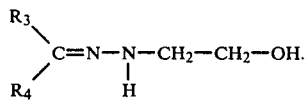
(XII)

The intermediate of formula XII is treated with propylene oxide and oxalic acid ethyl ester chloride, i.e.

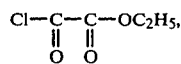

to yield the compound of the formula

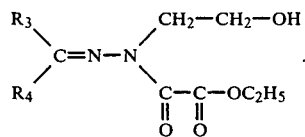
(XIII)

The intermediate of formula XIII is then treated with methylsulfonyl chloride to yield the compound of the formula

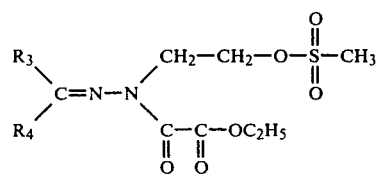
(XIV)

which is then treated in the presence of a crown ether with a lithium halide or sodium halide, preferably lithium bromide, to yield the compound of the formula

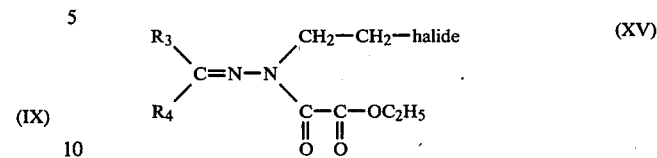
(XV)

Treatment of the compound of formula XV with an azide such as lithium azide, sodium azide, or tetramethylguanidinium azide yields the intermediate of formula VI.

The compounds of formula I wherein X is hydrogen,

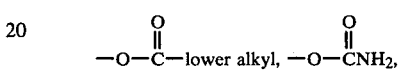

or heterothio can also be prepared by acylating a 7-amino cephalosporanic acid ester of formula IV with a compound of the formula

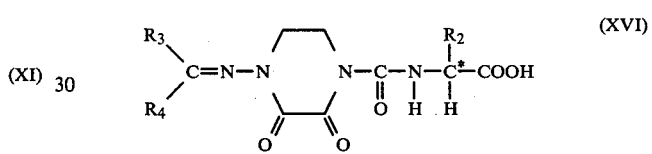
(XVI)

to yield the compounds of formula I in their ester form, i.e. R is t-butyl, benzyl, p-methoxybenzyl, p-nitrobenzyl, diphenylmethyl, 2,2,2-trichloroethyl, or trimethylsilyl. The ester protecting group can then be removed according to methods known in the art to yield the corresponding free acid compounds.

This acylation reaction can be performed directly with the acid of formula XVI by use of a coupling agent such as dicyclohexylcarbodiimide. Alternatively the acid compound of formula XVI can be converted to an activated derivative such as the acid chloride or bromide, an anhydride or mixed anhydride, or an activated ester formed according to methods known in the art.

The acid of formula XVI is prepared by reacting an α-amino acid of the formula

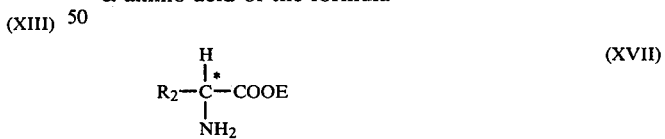
(XVII)

wherein E is hydrogen or a protecting group such as diphenylmethyl or p-nitrobenzyl, with the acid chloride of formula III. The protecting group can then be removed to yield the acid of formula XVI.

Also, when E is p-nitrobenzyl the resulting ester of formula XVI can be employed to directly acylate a desmethoxy 7-aminocephalosporanic acid ester of formula IV (i.e. $R_1$ is hydrogen) and yield the corresponding desmethoxy compound of formula I.

The compounds of formula Ia can be prepared by reacting a compound of formula I wherein R is hydrogen and X is

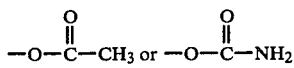

with pyridine or carbamoyl substituted pyridine in a polar solvent such as water and in the presence of a catalyst such as an alkali metal thiocyanate according to the procedures taught in U.S. Pat. No. 3,792,047 and German Offenlegungsschrift No. 2,234,280.

Similarly, the compounds of formula I wherein X is $N_3$ are prepared by reacting a compound of formula I wherein X is

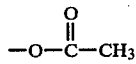

with sodium azide as taught in various U.S. Patents including U.S. Pat. Nos. 3,360,515; 3,658,802; 4,006,230; etc.

Also, the compounds of formula I wherein X is heterothio can be prepared by reacting the compound of formula I wherein R is hydrogen and X is

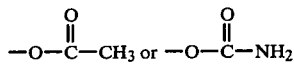

with mercaptan of the formula hetero-S-H             (XVIII)

or an alkali metal (preferably sodium) mercaptan salt of the formula hetero-S-alkali metal.     (XIX)

Such methods of introducing a heterothio group in the 3-position are disclosed in various U.S. Patents including U.S. Pat. Nos. 3,955,213; 4,066,762; etc.

The compounds of formula I wherein R and $R_9$ are sodium or potassium are prepared by reacting the corresponding free acid of formula I (R and $R_9$ are hydrogen) with the appropriate salt forming reactant.

The compounds of formula I wherein R is

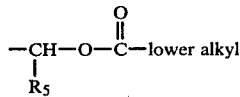

can be obtained by treating the corresponding free acid of formula I with one or two moles of a compound of the formula

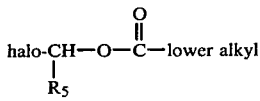
(XX)

wherein halo is chlorine or bromine in an inert solvent such as dimethylformamide at or below ambient temperature.

Similarly, the compounds of formula I wherein R is

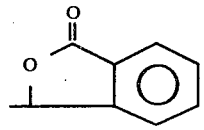

are prepared by treating the free acid compound of formula I with a compound of the formula

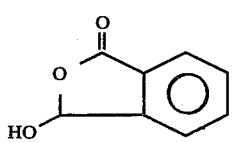
(XXI)

as taught by Ferres et al. in U.S. Pat. No. 3,860,579.

The compounds of formula I wherein $R_2$ is other than hydrogen are optically active due to the presence of an asymmetric carbon atom represented as C* in the preceding formulas. By selection of the appropriate starting material it is possible to obtain the compounds of formula I as a mixture of optically active isomers or isolated as a single isomer. The various optical isomers as well as their mixtures are within the scope of the invention.

Also, the compounds of formula I and the various intermediates wherein $R_2$ is 2-amino-4-thiazolyl are tautomeric and can be structurally represented as

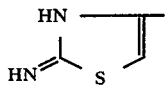

Though the 2-amino-4-thiazolyl form is being used throughout this application, both forms are within the scope of this invention.

Preferred compounds of this invention are those of formula I wherein R is hydrogen, sodium or potassium; $R_1$ is hydrogen; $R_2$ is phenyl, 2-thienyl, 3-thienyl, 2-furyl, 3-furyl, or 2-amino-4-thiazolyl; $R_3$ is methyl, phenyl, 2-thienyl, or 2-furyl; $R_4$ is hydrogen or methyl; X is hydrogen,

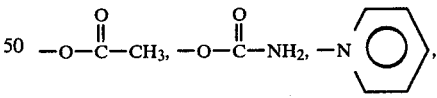

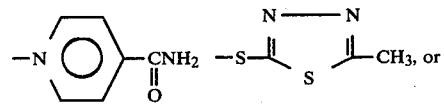

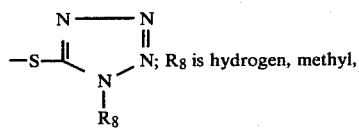; $R_8$ is hydrogen, methyl,

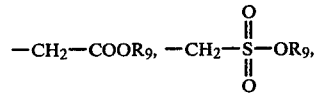

or —(CH$_2$)$_2$—N(CH$_3$)$_2$; and R$_9$ is hydrogen, sodium or potassium.

Most preferred are the above compounds wherein R$_3$ is phenyl and R$_4$ is hydrogen.

The compounds of formula I wherein R is hydrogen, sodium, potassium, —CH$_2$—O—lower alkyl,

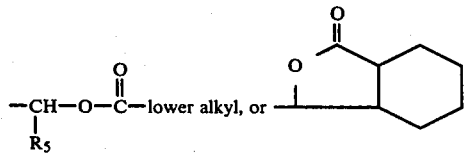

are useful antibacterial agents possessing activity against various gram-positive and gram-negative organisms such as *Staphylococcus aureus, Escherichia coli, Enterobacter cloacae, Klebsiella pneumoniae, Klebsiella aerogenes, Proteus rettgeri, Proteus vulgarius, Proteus mirabilis, Serratia marcescens, Salmonella typhosa, Shigella sonnei, Citrobacter freundii, Pseudomonas aeruginosa,* etc. They may be used as antibacterial agents to combat infections due to organisms such as those named above, and in general may be utilized in a manner similar to cephalotin and other cephalosporins. For example, a compound of formula I or a physiologically acceptable salt thereof may be used in various animal species in an amount of about 1 to 100 mg./kg., daily in oral or parenteral form, in single or two to four divided doses to treat infections of bacterial origin, e.g., 5.0 mg./kg. in mice.

Up to about 600 mg. of an acid compound of formula I or a physiologically acceptable salt thereof may be incorporated in an oral dosage form such as tablets, capsules or elixirs or in an injectable form in a sterile aqueous vehicle prepared according to conventional pharmaceutical practice.

Illustrative process details are provided in the examples for the various reactions. All temperatures are on the centigrade scale.

EXAMPLE 1

7β-[[D-[[[2,3-Dioxo-4-[(phenylmethylene)amino]-1-piperazinyl]carbonyl]amino]-2-thienylacetyl]-amino]-3-[[(1-methyl-1H-tetrazol-5-yl)thio]-methyl]-8-oxo-5-thia-1-azabicyclo[4.2.0]oct-2-ene-2-carboxylic acid (a) [1-(2-Hydroxyethyl)-2-(phenylmethylene)-hydrazino]oxoacetic acid, ethyl ester 8.2 g. of 2-[2-(phenylmethylene)hydrazino]ethanol are dissolved in 50 ml. of tetrahydrofuran. 5.6 g. of propylene oxide are added and then 7.5 g. (10% excess) of chlorooxoacetic acid ethyl ester are added dropwise at 0°. After three hours, the reaction mixture is concentrated in vacuo to yield a yellow oil which crystallizes after the addition of a small amount of toluene and overnight refrigeration. This material is filtered under suction and the residue is washed with petroleum ether to yield a light yellow powder. Recrystallization from carbon tetrachloride yields 7.6 g. of white crystalline [1-(2-hydroxyethyl)-2-(phenylmethylene)hydrazino]oxoacetic acid, ethyl ester; m.p. 96°-98°.

(b) [1-[2-[(Methylsulfonyl)oxy]ethyl]-2-(phenylmethylene)-hydrazino]oxoacetic acid, ethyl ester 26.4 g. of the ethyl ester product from part (a) and 10 g. of triethylamine are dissolved in 200 ml. of methylene chloride. 11.4 g. of methylsulfonyl chloride dissolved in a small amount of methylene chloride are added dropwise at −20°. After two hours, 300 ml. of water are added to the reaction solution and this mixture is stirred for 10 minutes. The organic phase is dried (Na$_2$SO$_4$) and, after distilling off the solvent, a colorless oil is obtained which crystallizes upon scratching. Recrystallization from ethanol yields as a white powder [1-[2-[(methylsulfonyl)oxy]ethyl]-2-(phenylmethylene)hydrazino]oxoacetic acid, ethyl ester; m.p. 93°-95°.

(c) [1-(2-Bromoethyl)-2-(phenylmethylene)hydrazino]oxoacetic acid, ethyl ester 3.4 g. of the ethyl ester product from part (b) are dissolved in 100 ml. of acetone. 1.3 g. (50% excess) of lithium bromide and 0.1 g. of 18-Crown-6 (1,4,7,10,13,16-hexaoxacyclooctadecane) are added and the mixture is stirred for three hours at 50°. After the reaction has been completed as determined by TLC, the solvent is distilled off and the reaction mixture is taken up in 50 ml. of methylene chloride and shaken with 50 ml. of water. The organic phase is dried and concentrated to yield the crude product as an oil which, after scratching, crystallizes in several hours. Recrystallization from isopropanol yields purified [1-(2-bromoethyl)-2-(phenylmethylene)hydrazino]-oxoacetic acid, ethyl ester; m.p. 56°-57°.

(d) [1-(2-Azidoethyl)-2-(phenylmethylene)hydrazino]oxoacetic acid, ethyl ester 11 g. of the ethyl ester product from part (c) are added to acetone along with 5.7 g. of tetramethylguanidinium azide and 0.05 g. of 18-Crown-6. The mixture is refluxed for eight hours. After distilling off the solvent, the reaction mixture is stirred with 50 ml. of methylene chloride. The organic phase, after drying and concentrating, leaves an oil which crystallizes in the form of white crystals upon the addition of a small amount of isopropanol to yield [1-(2-azidoethyl)-2-(phenylmethylene)hydrazino]oxoacetic acid, ethyl ester; m.p. 59°-61°.

(e) 1-[(Phenylmethylene)amino]-2,3-piperazinedione 2 g. of the ethyl ester product from part (d) are dissolved in 100 ml. of ethanol. 0.5 g. of Lindlar catalyst are added and the reaction mixture is stirred for four hours at room temperature under two atmospheres of hydrogen. At intervals the reaction mixture is filtered. After completion of the slow absorption of hydrogen, the reaction solution is flooded with nitrogen and then heated to a boil. This mixture is filtered while hot and after cooling 1 g. of crude product is obtained from the filtrate. Recrystallization from water yields as white crystals purified 1-[(phenylmethylene)amino]-2,3-piperazinedione; m.p. 229°-231°.

(f) 1-[(Phenylmethylene)amino]-4-(trimethylsilyl)-2,3-piperazinedione 2.1 g. of the piperazinedione product from part (e) are suspended in 50 ml. of acetonitrile. 1 g. of N-methyl-O-trimethylsilyltrifluoroacetamide are added and the mixture is refluxed for one hour. A clear solution forms and upon cooling to −10° there is obtained a thick white precipitate. NMR analysis of the precipitate indicates that it contains 1-[(phenylmethylene)amino]-4-(trimethylsilyl)-2,3-piperazinedione as the major product and about 25% by weight of 5,6-dihydro-1-[(phenylmethylene)amino]-3-[(trimethylsilyl)oxo]-2-(1H)-pyrazinone. The precipitate is filtered under suction, washed with petroleum ether, and dried under nitrogen; m.p. 190°–191°.

(g) 2,3-Dioxo-4-](phenylmethylene)amino]-1-piperazinecarbonyl chloride 4.2 g. of the mixture obtained from part (f) are dissolved in 50 ml. of methylene chloride and a solution of 40 mM of phosgene in methylene chloride is added dropwise at 0°. Over a period of four hours a thick precipitate forms. To ensure a complete reaction, the mixture is allowed to stand overnight under refrigeration. The mixture is then filtered and the residue is dried at 40° under a vacuum to yield as a white powder 5.9 g. of 2,3-dioxo-4-[(phenylmethylene)-amino]-1-piperazinecarbonyl chloride; m.p. 185° (dec.).

(h) 7β-[[D-[[[2,3-Dioxo-4-[(phenylmethylene)-amino]-1-piperazinyl]carbonyl]amino]-2-thienylacetyl]amino]-3-[[(1-methyl-1H-tetrazol-5-yl)-thio]methyl]-8-oxo-5-thia-1-azabicyclo[4.2.0]oct-2-ene-2-carboxylic acid 2.8 g. of 7β-[D-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt is suspended in 100 ml. of absolute acetonitrile. 2.5 g. of bistrimethylsilyl acetamide are added and after vigorous stirring for thirty minutes a clear solution is obtained. This solution is cooled to 0° and 0.5 g. of N-methylmorpholine are added followed by a crystal of 4-dimethylaminopyridine. Then 2 g. of 2,3-dioxo-4-[(phenylmethylene)amino]-1-piperazinecarbonyl chloride, from part (g), suspended in acetonitrile are added dropwise. After one hour, the reaction mixture is allowed to come to room temperature and 10 ml. of methanol are added. The mixture is stirred for thirty minutes and then distilled in vacuo at 40° until 20 ml. of solvent is distilled off. 200 ml. of water and 200 ml. of ethyl acetate are added to the residue. This mixture is cooled to 5° and acidified to a pH of 2.5 by the addition of 2 N phosphoric acid. This acidified mixture is stirred for 10 minutes, the organic phase is washed with 100 ml. of sodium chloride solution and water, and dried (Na$_2$SO$_4$). The ethyl acetate solution is concentrated to yield 1.6 g. of crude product. This crude product is dissolved in a small amount of tetrahydrofuran, treated with charcoal, and precipitated with ether/petroleum ether to yield as a light beige powder 7β-[[D-[[[2,3-dioxo-4-[(phenylmethylene)amino]-1-piperazinyl]-carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 162° (dec.).

EXAMPLE 2

7β-[[D-[[[2,3-Dioxo-4-[(phenylmethylene)-amino]-1-piperazinyl]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt (monohydrate)

400 mg. of the acid product from Example 1 are dissolved in 5 ml. of tetrahydrofuran and 2.8 ml. of 0.2 N sodium 2-ethyl hexanoate solution are added. After the addition of 3 ml. of isopropyl ether, the reaction mixture is stirred for twenty minutes and the precipitate is filtered under suction to yield as a beige powder 7β-[[D-[[[2,3-dioxo-4-[(phenylmethylene)amino]-1-piperazinyl]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt (monohydrate); m.p. 168° (dec.).

Similarly, by employing potassium ethyl hexanoate solution one obtains the corresponding potassium salt.

EXAMPLE 3

7β-[[D,L-[[[2,3-Dioxo-4-[(phenylmethylene)-amino]-1-piperazinyl]carbonyl]amino]-2-furylacetyl]amino]-3-[[(1-methyl-1H-tetrazol-5-yl)thio]methyl]-8-oxo-5-thia-1-azabicyclo[4.2.0]oct-2-ene-2-carboxylic acid Following the procedure of Example 1 but employing 7β-[D,L-2-amino-2-(2-furyl)-acetamido]-3-[[(1-methyl-1H-tetrazol-5-yl)-thio]methyl]-8-oxo-5-thia-1-azabicyclo[4.2.0]oct-2-ene-2-carboxylic acid, trifluoroacetic acid salt, one obtains as a beige powder 7β-[[D,L-[[[2,3-dioxo-4-[(phenylmethylene)amino]-1-piperazinyl]carbonyl]amino]-2-furylacetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 164° (dec.).

EXAMPLE 4

7β-[[D,L-[[[2,3-Dioxo-4-[(phenylmethylene)-amino]-1-piperazinyl]carbonyl]amino]-2-furylacetyl]amino]-3-[[(1-methyl-1H-tetrazol-5-yl)thio-methyl]-8-oxo-5-thia-1-azabicyclo[4.2.0]oct-2-ene-2-carboxylic acid, sodium salt The acid product from Example 3 is treated with sodium 2-ethyl hexanoate according to the procedure of Example 2 to yield as a beige powder 7β-[[D,L-[[[2,3-dioxo-4-[(phenylmethylene)amino]-1-piperazinyl]-carbonyl]amino]-2-furylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; m.p. 172° (dec.).

Similarly, by employing potassium ethyl hexanoate one obtains the corresponding potassium salt.

EXAMPLE 5

3-[(Acetyloxy)methyl]-7β-[[D,-[[[2,3-dioxo-4-[(phenylmethylene)amino]-1-piperazinyl]-carbonyl]amino]-2-thienylacetyl]amino]-8-oxo-5-thia-1-azabicyclo[4.2.0]oct-2-ene-2-carboxylic acid Following the procedure of Example 1 but employing 3-[(acetyloxy)methyl]-7β-[D-2-amino-2-(2-thienyl)acetamido]-8-oxo-5-thia-1-azabicyclo[4.2.0]oct-2-ene-2-carboxylic acid, trifluoroacetic acid salt and substituting propylene oxide for the N-methylmorpholine, one obtains as a beige powder 3-[(acetyloxy)methyl]-7β-[[-D-[[[2,3-dioxo-4-[(phenylmethylene]amino]-1-piperazinyl]carbonyl]amino]-2-thienylacetyl]amino]-8-oxo-5-thia-1-azabicyclo[4.2.0]oct-2-ene-2-carboxylic acid; m.p. 148° (dec.).

EXAMPLE 6

3-[(Acetyloxy)methyl]-7β-[[D-[[[2,3-dioxo-4-[(phenylmethylene)amino]-1-piperazinyl]-carbonyl]amino]-2-thienylacetyl]amino]-8-oxo-5-thia-1-azabicyclo[4.2.-0]oct-2-ene-2-carboxylic acid, sodium salt (dihydrate)

The acid product from Example 5 is treated with sodium 2-ethyl hexanoate according to the procedure of Example 2 to yield 3-[(acetyloxy)methyl]-7β-[[D-[[[2,3-dioxo-4-[(phenylmethylene)amino]-1-piperazinyl]carbonyl]amino]-2-thienylacetyl]amino]-8-oxo-5-thia-1-azabicyclo[4.2.0]oct-2-ene-2-carboxylic acid, sodium salt (dihydrate); m.p. 151° (dec.).

Similarly, by employing potassium ethyl hexanoate one obtains the corresponding potassium salt.

EXAMPLE 7

7β-[[D-[[[2,3-Dioxo-4-[(phenylmethylene)amino]-1-piperazinyl]carbonyl]amino]phenylacetyl]-amino]-3-[[(1-methyl-1H-tetrazol-5-yl)thio]-methyl]-8-oxo-5-thia-1-azabicyclo[4.2.0]oct-2-ene-2-carboxylic acid (monohydrate)

Following the procedure of Example 1 but employing 7β-[D-2-amino-2-(phenyl)acetamido]-3-[[(1-methyl-1H-tetrazol-5-yl)thio]-methyl]-8-oxo-5-thia-1-azabicyclo[4.2.0]oct-2-ene-2-carboxylic acid, trifluoroacetic acid salt and substituting propylene oxide for the N-methylmorpholine, one obtains as a beige powder 7β-[[D-[[[2,3-dioxo-4-[(phenylmethylene)amino]-1-piperazinyl]carbonyl]amino]-phenylacetyl]amino]-3-[[(1-methyl-1H-tetrazol-5-yl)thio]methyl]-8-oxo-5-thia-1-azabicyclo[4.2.0]oct-2-ene-2-carboxylic acid (monohydrate); m.p. 157° (dec.).

EXAMPLE 8

7β-[[D-[[[2,3-Dioxo-4-[(phenylmethylene)amino]-1-piperazinyl]carbonyl]amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt (dihydrate)

The acid product from Example 7 is treated with sodium 2-ethyl hexanoate according to the procedure of Example 2 to yield 7β-[[D-[[[2,3-dioxo-4-[(phenylmethylene)amino]-1-piperazinyl]carbonyl]amino]-phenylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt (dihydrate); m.p. 167°.

Similarly, by employing potassium ethyl hexanoate one obtains the corresponding potassium salt.

EXAMPLE 9

7β-[[D-[[[2,3-Dioxo-4-[(phenylmethylene)amino]-1-piperazinyl]carbonyl]amino]-2-thienylacetyl]-amino]-3-[[(2-methyl-1,3,4-thiadiazol-5-yl)thio]methyl]-8-oxo-5-thia-1-azabicyclo[4.2.0]oct-2-ene-2-carboxylic acid Following the procedure of Example 1 but employing 7β-[D-2-amino-2-(2-thienyl)-acetamido]-3-[[(2-methyl-1,3,4-thiadiazol-5-yl)thio]methyl]-8-oxo-5-thia-1-azabicyclo[4.2.0]oct-2-ene-2-carboxylic acid, trifluoroacetic acid salt and substituting propylene oxide for the N-methylmorpholine, one obtains 7β-[[D-[[[2,3-dioxo-4-[(phenylmethylene)-amino]-1-piperazinyl]carbonyl]amino]-2-thienylacetyl]amino]-3-[[(2-methyl-1,3,4-thiadiazol-5-yl)thio]methyl]-8-oxo-5-thia-1-azabicyclo[4.2.0]oct-2-ene-2-carboxylic acid; m.p. 122° (dec.).

By reacting the above acid with sodium ethyl hexanoate or potassium ethyl hexanoate, one obtains the corresponding sodium or potassium salt.

EXAMPLES 10–50

Following the procedure of Example 1 but employing the piperazinecarbonyl chloride shown in Col. I and the trifluoroacetic acid salt shown in Col. II, one obtains the product shown in Col. III.

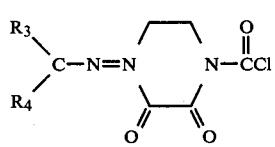

Col. I

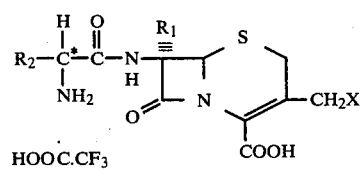

Col. II

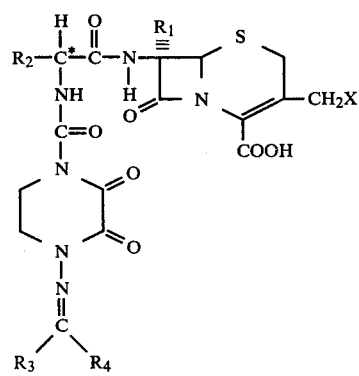

Col. III

| Ex. | X | $R_1$ | $R_2$ | $R_3$ | $R_4$ |
|---|---|---|---|---|---|
| 10 | | —H | | | —H |

-continued

| Ex. | X | R₁ | R₂ | R₃ | R₄ |
|-----|---|-----|-----|-----|-----|
| 11 | 1-methyl-tetrazol-5-yl-thio | —OCH₃ | 2-thienyl | phenyl | —H |
| 12 | —O—C(=O)—CH₃ | —H | 2-(2-amino-thiazol-4-yl) | phenyl | —H |
| 13 | 1-(carboxymethyl)-tetrazol-5-yl-thio | —H | 2-thienyl | phenyl | —H |
| 14 | 1-(sulfomethyl)-tetrazol-5-yl-thio | —H | 2-furyl | phenyl | —H |
| 15 | 1-[2-(dimethylamino)ethyl]-tetrazol-5-yl-thio | —H | phenyl | phenyl | —H |
| 16 | —O—C(=O)—NH₂ | —H | 2-thienyl | phenyl | —H |
| 17 | —O—C(=O)—NH₂ | —OCH₃ | 2-furyl | phenyl | —H |
| 18 | 4-methyl-thiazol-2-yl-thio | —H | 2-(2-amino-thiazol-4-yl) | phenyl | —H |
| 19 | 4-methyl-thiazol-2-yl-thio | —H | 4-hydroxyphenyl | phenyl | —H |
| 20 | 4-methyl-thiazol-2-yl-thio | —H | 3-methyl-2-thienyl | phenyl | —H |
| 21 | 5-methyl-1,3,4-oxadiazol-2-yl-thio | —H | 3-chloro-2-thienyl | phenyl | —H |
| 22 | 1,2,3-thiadiazol-5-yl-thio | —OCH₃ | 2-thienyl | phenyl | —CH₃ |
| 23 | pyridin-2-yl-thio N-oxide | —H | 2-thienyl | phenyl | —H |

-continued

| Ex. | X | $R_1$ | $R_2$ | $R_3$ | $R_4$ |
|---|---|---|---|---|---|
| 24 | $-O-\overset{O}{\underset{\|}{C}}-C_2H_5$ | $-H$ | $\text{C}_6\text{H}_5-CH_2-$ | $-C_6H_5$ | $-H$ |
| 25 | $-O-\overset{O}{\underset{\|}{C}}-CH_3$ | $-H$ | $\text{C}_6\text{H}_5-(CH_2)_2-$ | $-C_6H_5$ | $-H$ |
| 26 | $-O-C_2H_5$ | $-H$ | 3-Cl-C$_6$H$_4$-CH$_2$- | $-C_6H_5$ | $-H$ |
| 27 | $-H$ | $-H$ | 4-CH$_3$O-C$_6$H$_4$- | $-C_6H_5$ | $-H$ |
| 28 | $-H$ | $-H$ | 5-Br-thien-2-yl | $-C_6H_5$ | $-CH_3$ |
| 29 | 1-methyl-1H-tetrazol-5-ylthio | $-H$ | 4-pyridyl | $-CH_3$ | $-H$ |
| 30 | $-O-\overset{O}{\underset{\|}{C}}-CH_3$ | $-H$ | 3-pyridyl | $-C_6H_5$ | $-H$ |
| 31 | 1-ethyl-1H-tetrazol-5-ylthio | $-H$ | $-C_2H_5$ | 4-CH$_3$-C$_6$H$_4$- | $-H$ |
| 32 | $-O-\overset{O}{\underset{\|}{C}}-CH_3$ | $-H$ | cyclobutyl | $-C_6H_5$ | $-H$ |
| 33 | 1-methyl-1H-tetrazol-5-ylthio | $-H$ | cyclohexenyl | $-C_6H_5$ | $-H$ |
| 34 | 5-methyl-1,3,4-thiadiazol-2-ylthio | $-H$ | cyclohexyl | $-C_6H_5$ | $-H$ |
| 35 | 1H-1,2,3-triazol-5-ylthio | $-OCH_3$ | 3-Cl-furan-2-yl | 4-HO-C$_6$H$_4$- | $-CH_3$ |
| 36 | $-O-\overset{O}{\underset{\|}{C}}-CH_3$ | $-H$ | 2-amino-thiazol-4-yl | $-CH_2-C_6H_5$ | $-H$ |
| 37 | 1-methyl-1H-tetrazol-5-ylthio | $-H$ | thien-2-yl | $-(CH_2)_2-C_6H_5$ | $-H$ |

-continued

| Ex. | X | R₁ | R₂ | R₃ | R₄ |
|---|---|---|---|---|---|
| 38 | $-S-\underset{\underset{CH_3}{N}}{\overset{N=N}{\underset{\|}{C}}}\!\!\!\diagdown\!\!\!N$ (1-methyl-tetrazol-5-yl-thio) | $-H$ | 2-furyl | $-CH_2-C_6H_4-Cl$ (p) | $-CH_3$ |
| 39 | $-O-\overset{O}{\underset{\|}{C}}-CH_3$ | $-H$ | 2-thienyl | $-C_2H_5$ | $-H$ |
| 40 | $-O-\overset{O}{\underset{\|}{C}}-CH_3$ | $-H$ | 2-amino-4-thiazolyl | $-CH_3$ | $-CH_3$ |
| 41 | $-O-\overset{O}{\underset{\|}{C}}-NH_2$ | $-H$ | phenyl | $-t-C_4H_9$ | $-H$ |
| 42 | $-S-\underset{\underset{H}{N}}{\overset{N=N}{\underset{\|}{C}}}\!\!\!\diagdown\!\!\!N$ (1H-tetrazol-5-yl-thio) | $-OCH_3$ | 2-pyridyl | $-C_2H_5$ | $-C_2H_5$ |
| 43 | $-O-\overset{O}{\underset{\|}{C}}-CH_3$ | $-H$ | 2-amino-4-thiazolyl | 2-thienyl | $-H$ |
| 44 | $-S-\underset{\underset{CH_3}{N}}{\overset{N=N}{\underset{\|}{C}}}\!\!\!\diagdown\!\!\!N$ | $-H$ | 2-thienyl | 2-thienyl | $-CH_3$ |
| 45 | $-O-\overset{O}{\underset{\|}{C}}-CH_3$ | $-H$ | 2-amino-4-thiazolyl | 2-furyl | $-H$ |
| 46 | $-S-\underset{S}{\overset{N=N}{\underset{\|}{C}}}\!\!\!-CH_3$ (5-methyl-1,3,4-thiadiazol-2-yl-thio) | $-H$ | 2-thienyl | 2-furyl | $-CH_3$ |
| 47 | $-S-\underset{\underset{H}{N}}{\overset{N=N}{\underset{\|}{C}}}\!\!\!\diagdown\!\!\!N$ | $-OCH_3$ | phenyl | 5-chloro-2-thienyl | $-H$ |
| 48 | $-O-\overset{O}{\underset{\|}{C}}-CH_3$ | $-H$ | phenyl | 2-furyl | $-H$ |
| 49 | $-O-\overset{O}{\underset{\|}{C}}-CH_3$ | $-H$ | 2-amino-4-thiazolyl | 2-thienyl | $-CH_3$ |
| 50 | $-O-\overset{O}{\underset{\|}{C}}-CH_3$ | $-H$ | 2-amino-4-thiazolyl | 2-thienyl | $-CH_3$ |

The compounds of Examples 10–50 are obtained as the D-, L-, or a mixture of the D- and L- isomers depending upon the optical activity of the starting material of Col. II.

The final compounds can be converted to the corresponding sodium or potassium salt as taught in Example 2. In the case of the compounds of Examples 13 and 14, the disodium or dipotassium salt would be obtained.

Also, the acid products of Examples 1,3,5,7, and 9 to 50 can be converted to an ester form according to known methods as set forth in the specification.

EXAMPLE 51

3-[[4-(Aminocarbonyl)pyridino]methyl]-7β-[[D-[[[2,3-dioxo-4-[(phenylmethylene)amino]-1-piperazinyl]carbonyl]amino]-2-thienylacetyl]-amino]-8-oxo-5-thia-1-azabicyclo[4.2.0]oct-2-ene-2-carboxylic acid A mixture of 0.005 mole of the sodium salt product of Example 6, 0.0075 mole of 4-pyridinecarboximide, 12 g. of potassium thiocyanate, and 7.5 ml. of water are heated at 50° for 24 hours. The resulting solution is passed through a chromatography column filled with ion exchanger Amberlite XAD-2. The column is washed with water and the titled compound is eluted with a mixture of water:methanol (8:2). The methanol is evaporated from the eluate and the aqueous solution is lyophilized. The amorphous residue is triturated with ether and filtered under suction to yield 3-[[4-(aminocarbonyl)pyridino]methyl]-7β-[[D-[[[2,-3-dioxo-4-[(phenylmethylene)amino]-1-piperazinyl]carbonyl]amino]-2-thienylacetyl]amino]-8-oxo-5-thia-1-azabicyclo[4.2.0]oct-2-ene-2-carboxylic acid.

EXAMPLES 52-65

Following the procedure of Example 51 but employing the cephalosporanic acid sodium salt shown in Col. I and the pyridine compound shown in Col. II, one obtains the product shown in Col. III.

Col. I

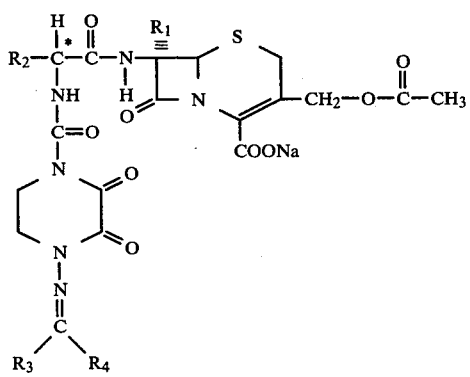

Col. II

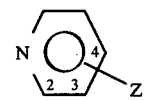

Col. III

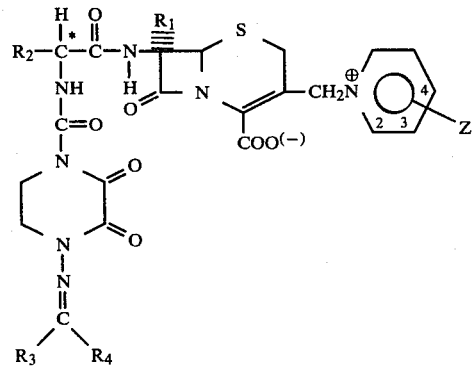

| Ex. | $R_1$ | $R_2$ | $R_3$ | $R_4$ | Z |
|---|---|---|---|---|---|
| 52 | —H | (furan) | (phenyl) | —H | $-\overset{O}{\underset{\|}{C}}NH_2$ (4) |
| 53 | —H | (2-aminothiazole) | (phenyl) | —H | $-\overset{O}{\underset{\|}{C}}NH_2$ (4) |
| 54 | —H | (phenyl) | (phenyl) | —H | $-\overset{O}{\underset{\|}{C}}NH_2$ (4) |

-continued

| Ex. | $R_1$ | $R_2$ | $R_3$ | $R_4$ | Z |
|---|---|---|---|---|---|
| 55 | —H | 2-thienyl | phenyl | —CH$_3$ | —H |
| 56 | —OCH$_3$ | 2-thienyl | phenyl | —H | —H |
| 57 | —H | 2-amino-4-thiazolyl | phenyl | —H | —H |
| 58 | —OCH$_3$ | 2-thienyl | —CH$_3$ | —CH$_3$ | —CNH$_2$ (3) |
| 59 | —H | 4-hydroxyphenyl | 2-thienyl | —H | —CNH$_2$ (4) |
| 60 | —H | 2-methyl-2-thienyl | 2-furyl | —CH$_3$ | —H |
| 61 | —H | 2-pyridyl | 2-furyl | —H | —H |
| 62 | —H | phenyl | 4-chlorophenyl | —H | —CNH$_2$ (2) |
| 63 | —OCH$_3$ | 2-thienyl | —CH$_2$-phenyl | —H | —CNH$_2$ (4) |
| 64 | —H | 2-amino-4-thiazolyl | —CH$_3$ | —CH$_3$ | —CNH$_2$ (4) |
| 65 | —H | 2-amino-4-thiazolyl | —C$_2$H$_5$ | —H | —H |

The compounds of Examples 52 to 65 are obtained as the D-, L-, or a mixture of D- and L-isomers depending upon the optical activity of the starting cephalosporin shown in Col. I.

Similarly, by reacting the sodium salt of Example 6 or those shown in Col. I of Examples 52 to 65 with sodium azide according to the procedure set forth in Example 1 of U.S. Pat. No. 3,658,802, other compounds within the scope of the invention are obtained.

EXAMPLE 66

7β-[[D-[[[2,3-Dioxo-4-[(phenylmethylene)amino ]-1-piperazinyl]carbonyl]amino]-2-thienylacetyl]-amino]-3-[[(1-methyl-1H-tetrazol-5-yl)thio]-methyl]-8-oxo-5-thia-1-azabicyclo[4.2.0]oct-2-ene-2-carboxylic acid, sodium salt The product of Example 2 can also be prepared according to the following procedure.

0.002 mol. of the sodium salt product of Example 6 is brought into solution in 100 ml. of a phosphate buffer at a pH of 6.4. Then 0.0024 mol. of 1-methyl-1H-tetrazolyl-2-thiol is added. The solution is heated at 60° for six hours. After cooling, the pH is adjusted to 7.0 and the solution is chromatographed on the ion exchange resin Amberlite XAD-2. The fraction containing the desired product is freeze dried to yield 7β-[[D-[[[2,3-dioxo-4-[(phenylmethylene)amino]-1-piperazinyl]carbonyl]-amino]-2-thienylacetyl]amino]-3-[[(1-methyl-1H tetrazol-5-yl)thio]methyl]-8-oxo-5-thia-1-azabicyclo[4.2.-0]oct-2-ene-2-carboxylic acid, sodium salt.

EXAMPLES 67–82

Following the procedure of Example 66 but employing the cephalosporanic acid sodium salt shown in Col. I and the thiol shown in Col. II, one obtains the product shown in Col. III.

Col. I

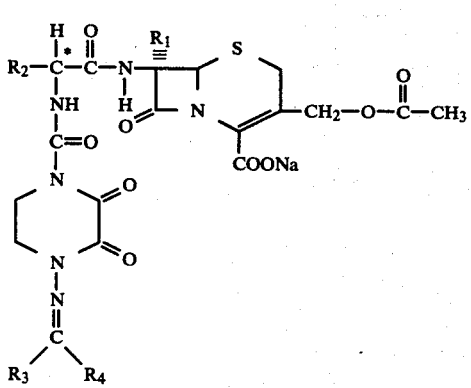

Col. II

HS—hetero

Col. III

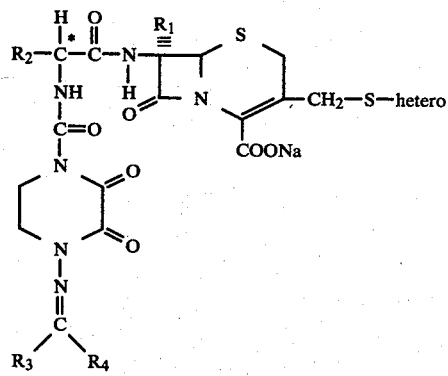

| Ex. | R₁ | R₂ | R₃ | R₄ | hetero |
|---|---|---|---|---|---|
| 67 | —OCH₃ | (thienyl) | (phenyl) | —H | (1-methyl-tetrazol-5-yl) |
| 68 | —H | (phenyl) | (phenyl) | —CH₃ | (1-methyl-tetrazol-5-yl) |
| 69 | —H | (furyl) | (phenyl) | —H | (1-methyl-tetrazol-5-yl) |
| 70 | —H | (2-amino-thiazol-4-yl) | (phenyl) | —H | (1-methyl-tetrazol-5-yl) |
| 71 | —OCH₃ | (5-chloro-thienyl) | (thienyl) | —H | (5-methyl-1,3,4-thiadiazol-2-yl) |
| 72 | —H | (furyl) | (5-methyl-thienyl) | —H | (5-methyl-1,3,4-thiadiazol-2-yl) |
| 73 | —H | (benzyl) | (furyl) | —H | (5-methyl-1,3,4-thiadiazol-2-yl) |
| 74 | —OCH₃ | (thienyl) | —CH₃ | —CH₃ | (1H-1,2,3-triazol-4-yl) |

-continued

| Ex. | R$_1$ | R$_2$ | R$_3$ | R$_4$ | hetero |
|-----|-------|-------|-------|-------|--------|
| 75 | —H | 4-pyridyl | —CH$_2$—phenyl | —H | 2-methyl-1,3,4-oxadiazol-5-yl |
| 76 | —H | cyclohexenyl | phenyl | —H | 1,3,4-thiadiazol-2-yl |
| 77 | —H | 2-aminothiazol-4-yl | 2-thienyl | —H | 1,3,4-thiadiazol-2-yl |
| 78 | —H | 2-thienyl | phenyl | —H | pyridine-N-oxide |
| 79 | —H | 2-thienyl | phenyl | —H | 1-(CH$_2$COONa)-tetrazol-5-yl |
| 80 | —H | 2-aminothiazol-4-yl | phenyl | —H | 1-(CH$_2$SO$_3$Na)-tetrazol-5-yl |
| 81 | —H | 2-aminothiazol-4-yl | phenyl | —H | 1-((CH$_2$)$_2$N(CH$_3$)$_2$)-tetrazol-5-yl |
| 82 | —OCH$_3$ | 2-furyl | phenyl | —H | 1-((CH$_2$)$_2$N(CH$_3$)$_2$)-tetrazol-5-yl |

The compounds of Examples 67 to 82 are obtained as the D-, L-, or a mixture of D- and L-isomers depending upon the optical activity of the starting cephalosporin shown in Col. I.

What is claimed is:
1. A compound of the formula

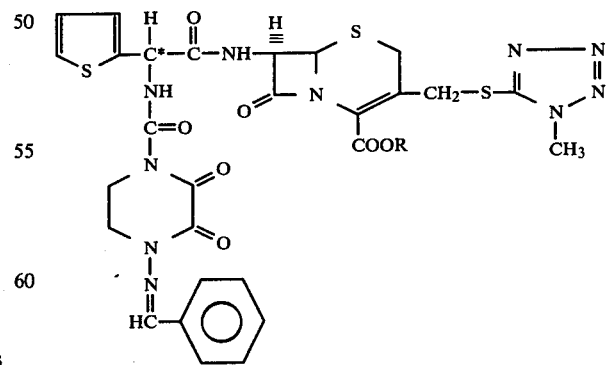

wherein R is hydrogen, sodium or potassium.
2. The compound of claim 1, 7β-[[D-[[[2,3-dioxo-4--[(phenylmethylene)amino]-1-piperazinyl]carbonyl-]amino]-2-thienylacetyl]-amino]-3-[[(1-methyl-1H-tetrazol-5-yl)thio]-methyl]-8-oxo-5-thia-1-azabicyclo[4.2.-0]oct-2-ene-2-carboxylic acid.

3. The sodium salt of the compound of claim 2.

4. A compound of the formula

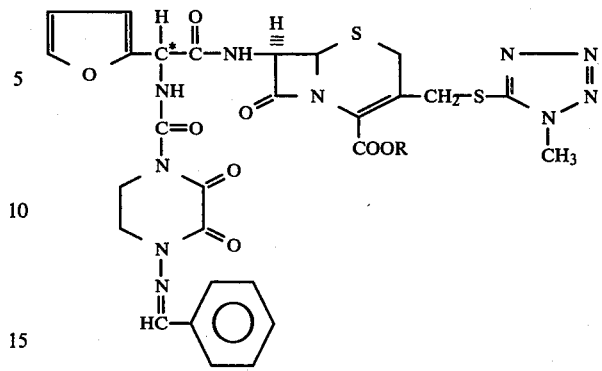

wherein R is hydrogen, sodium or potassium.

5. The compound of claim 4, 7β-[[D,-L-[[[2,3-dioxo--4-[(phenylmethylene)amino]-1-piperazinyl]carbonyl-]amino]-2-furylacetyl]-amino]-3-[[(1-methyl-1H-tetrazol-5-yl)thio]-methyl]-8-oxo-5-thia-1-azabicyclo[4.2.-0]oct-2-ene-2-carboxylic acid.

6. The sodium salt of the compound of claim 5.

* * * * *

UNITED STATES PATENT AND TRADEMARK OFFICE
CERTIFICATE OF CORRECTION

PATENT NO. : 4,386,199
DATED : May 31, 1983
INVENTOR(S) : Uwe D. Treuner, Hermann Breuer It is certified that error appears in the above-identified patent and that said Letters Patent are hereby corrected as shown below:

Column 9, lines 7-13, the second formula should read:

-- 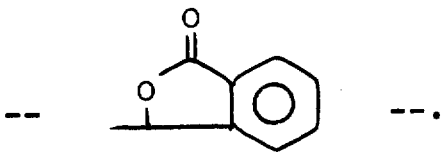 --.

Signed and Sealed this

Fourth Day of October 1983

[SEAL]

Attest:

Attesting Officer

GERALD J. MOSSINGHOFF

Commissioner of Patents and Trademarks